US008972459B2

(12) United States Patent  (10) Patent No.: US 8,972,459 B2
Chaliparambil et al.  (45) Date of Patent: Mar. 3, 2015

(54) DATA CHANGE TRACKING AND EVENT NOTIFICATION

(75) Inventors: Kishore R. Chaliparambil, Snoqualmie, WA (US); Chi Kit Chan, Bellevue, WA (US); Imran Mohiuddin, Redmond, WA (US); Bryan Dove, Seattle, WA (US); Mehul Y. Shah, Redmond, WA (US); Umesh Madan, Bellevue, WA (US); Ali Emami, Seattle, WA (US); Robert A. May, Redmond, WA (US); Eric Gunnerson, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 0 days.

(21) Appl. No.: 13/206,316

(22) Filed: Aug. 9, 2011

(65) Prior Publication Data

US 2013/0007069 A1  Jan. 3, 2013

Related U.S. Application Data

(63) Continuation of application No. 13/172,889, filed on Jun. 30, 2011, now Pat. No. 8,818,944.

(51) Int. Cl.
*G06F 17/30* (2006.01)
*G06Q 10/10* (2012.01)
*G06Q 50/22* (2012.01)

(52) U.S. Cl.
CPC ............... *G06Q 10/10* (2013.01); *G06Q 50/22* (2013.01)
USPC ........................................................ 707/803

(58) Field of Classification Search
USPC ................................................ 707/803, 625
See application file for complete search history.

(56) References Cited

U.S. PATENT DOCUMENTS

| 6,101,493 | A | * | 8/2000 | Marshall et al. ...................... 1/1 |
| 6,134,543 | A | * | 10/2000 | Witkowski et al. .................. 1/1 |
| 6,175,837 | B1 | * | 1/2001 | Sharma et al. ........................ 1/1 |
| 6,446,086 | B1 | | 9/2002 | Bartlett et al. |
| 6,546,402 | B1 | * | 4/2003 | Beyer et al. .................. 707/625 |
| 6,882,993 | B1 | | 4/2005 | Lawande et al. |
| 7,216,133 | B2 | * | 5/2007 | Wu et al. ...................... 707/620 |
| 7,277,900 | B1 | | 10/2007 | Ganesh et al. |
| 7,439,856 | B2 | * | 10/2008 | Weiner et al. ............ 340/539.12 |
| 8,032,397 | B2 | | 10/2011 | Lawless |

(Continued)

OTHER PUBLICATIONS

Luo, et al., "Content-Based Filtering for Efficient Online Materialized View Maintenance", Retrieved at <<http://pages.cs.wisc.edu/~gangluo/detect_cikm08.pdf >>, Proceeding of the 17th ACM conference on Information and knowledge management, Oct. 26-30, 2008, pp. 10.

(Continued)

*Primary Examiner* — Noosha Arjomandi
(74) *Attorney, Agent, or Firm* — Damon Rieth; Jim Ross; Micky Minhas

(57) ABSTRACT

The described implementations relate to updating views in a database system. One implementation can identify an active view that retrieves records from a database and determine one or more physical tables in the database that are referenced by the active view. The implementation can track one or more columns in the physical tables that are used by the active view and identify a change to the physical tables in a transaction log of the database. If the change does not affect the one or more columns, the change can be treated as an ignorable change for the active view.

20 Claims, 7 Drawing Sheets

(56) References Cited

U.S. PATENT DOCUMENTS

| | | | |
|---|---|---|---|
| 8,041,749 B2 | 10/2011 | Beck | |
| 8,065,269 B2* | 11/2011 | Nica et al. | 707/625 |
| 2002/0091827 A1 | 7/2002 | King et al. | |
| 2004/0073453 A1 | 4/2004 | Nenov et al. | |
| 2004/0098425 A1 | 5/2004 | Wiss et al. | |
| 2004/0172284 A1 | 9/2004 | Sullivan et al. | |
| 2005/0049993 A1 | 3/2005 | Nori et al. | |
| 2005/0097078 A1 | 5/2005 | Lohman et al. | |
| 2005/0102326 A1* | 5/2005 | Peleg et al. | 707/200 |
| 2005/0187797 A1 | 8/2005 | Johnson | |
| 2005/0208941 A1 | 9/2005 | Ordille et al. | |
| 2005/0209990 A1 | 9/2005 | Ordille et al. | |
| 2006/0155581 A1 | 7/2006 | Eisenberger et al. | |
| 2006/0178910 A1 | 8/2006 | Eisenberger et al. | |
| 2007/0013511 A1 | 1/2007 | Weiner et al. | |
| 2007/0041626 A1 | 2/2007 | Weiss et al. | |
| 2007/0226264 A1 | 9/2007 | Luo et al. | |
| 2008/0255885 A1 | 10/2008 | Eisenberger et al. | |
| 2009/0031327 A1 | 1/2009 | Nesamoney et al. | |
| 2009/0150172 A1 | 6/2009 | Duffey-Rosenstein et al. | |
| 2009/0216789 A1 | 8/2009 | Chowdhary et al. | |
| 2009/0313049 A1 | 12/2009 | Joao et al. | |
| 2010/0082370 A1* | 4/2010 | Frederick et al. | 705/3 |
| 2010/0161555 A1 | 6/2010 | Nica et al. | |
| 2010/0191546 A1* | 7/2010 | Kanamarlapudi et al. | 705/3 |
| 2010/0251153 A1 | 9/2010 | SanGiovanni et al. | |
| 2011/0040745 A1* | 2/2011 | Zaydman et al. | 707/714 |
| 2012/0022893 A1 | 1/2012 | Findlay et al. | |
| 2012/0173267 A1 | 7/2012 | Omidi | |
| 2012/0173490 A1 | 7/2012 | Gould et al. | |
| 2012/0221523 A1* | 8/2012 | Bendakovsky et al. | 707/640 |
| 2013/0006664 A1 | 1/2013 | Chaliparambil | |
| 2013/0006963 A1 | 1/2013 | Chaliparambil | |
| 2013/0117313 A1* | 5/2013 | Miao et al. | 707/781 |

OTHER PUBLICATIONS

Srivastava, et al., "Enabling Real Time Data Analysis", Retrieved at <<http://www.comp.nus.edu.sg/~vldb2010/proceedings/files/papers/K01.pdf>>, Proceedings of the VLDB Endowment, vol. 3 No. 1, Sep. 2010, pp. 1-2.

Lashley, Wayne, "Legacy Data Migration", Retrieved at <<http://www.treehouse.com/downloads/TREETIMES13.pdf>>, Aug. 13, 2006, pp. 1-8.

Lomet David B., "Data Engineering", Retrieved at <<http://citeseerx.ist.psu.edu/viewdoc/download?doi=10.1.1.107.4201&rep=rep1&type=pdf#page=31 , vol. 18 No. 2 Jun. 1995, pp. 52.

"Non-Final Office Action for U.S. Appl. No. 13/172,889", Filed date: Jun. 30, 2011, Mailed Date: Nov. 23, 2012, 19 pages.

"Response to Non-Final Office Action for U.S. Appl. No. 13/172,889", Mailed Date: Nov. 23, 2012, Filed Date: Mar. 20, 2013, 12 pages.

"Notice of Allowance and Examiner's Amendment for U.S. Appl. No. 13/172,889", Mailed date: Jun. 12, 2013, 14 pages.

"Amendment after Allowance for U.S. Appl. No. 13/172,889", Mailed Date: Jun. 12, 2013, Filed Date: Jul. 9, 2013, 8 pages.

"Response to Amendment after Allowance for U.S. Appl. No. 13/172,889", Mailed Date: Jun. 12, 2013, Filed Date: Aug. 29, 2013, 1 page.

"Request for Continued Examination for U.S. Appl. No. 13/172,889", Filed Date: Sep. 5, 2013, 3 pages.

"Notice of Allowance and Examiner's Amendment for U.S. Appl. No. 13/172,889", Mailed Date: Feb. 14, 2014, 14 pages.

"Non-Final Office Action for U.S. Appl. No. 13/206,365", Filed date: Aug. 9, 2011, Mailed date: Jan. 16, 2013, 18 pages.

"Response to Non-Final Office Action for U.S. Appl. No. 13/206,365", Mailed Date: Jan. 16, 2013, Filed Date: May 16, 2013, 12 pages.

"Final Office Action for U.S. Appl. No. 13/206,365", Filed date: Aug. 9, 2011, Mailed date: Jul. 17, 2013, 24 pages.

"Request for Continued Examination and Response to Final Office Action for U.S. Appl. No. 13/206,365", Mailed Date: Jul. 17, 2013, Filed Date: Oct. 25, 2013, 17 pages.

"Office Action Issued in U.S. Appl. No. 13/206,365", Mailed Date: Sep. 10, 2014, 26 pages.

* cited by examiner

FIG. 6A

Name: Dr. Jones    Subscription Name: Routine ER Visit

NOTIFY ON CORRELATED CONCEPTS?

Predefined Concept 1: NSAIDs (601)    [X] (603)

Predefined Concept 2: Pain (602)    [ ] (604)

Submit (605)

GUI 600

FIG. 6B

Name: Dr. Jones    Subscription Name: Fever ER Visit

NOTIFY ON CORRELATED CONCEPTS?

Predefined Concept 1: NSAIDs (601)    [X] (603)

Keyword Concept 2: Fever (606)    [X] (604)

Submit (605)

GUI 600

DATA CHANGE TRACKING AND EVENT NOTIFICATION

CROSS-REFERENCE TO RELATED APPLICATIONS

This patent application is a continuation of, and claims priority from, U.S. patent application Ser. No. 13/172,889 filed on Jun. 30, 2011, which is incorporated herein by reference in its entirety.

BACKGROUND

Modern databases can store extraordinary amounts of data, often organized in a multitude of different tables. Users can define view queries on these tables that allow the users to distill certain data of interest from the database. However, depending on various factors, the view queries can be very computationally intensive and can tend to strain resources by increasing processor load, memory utilization, disk accesses, etc.

For example, some view queries are relatively complex, and may access a large number of tables. Moreover, often there are many different view queries being executed frequently by different users. The computational load caused by complex view queries and/or large numbers of view queries can be compounded by frequent database record updates, because the views generally need to be refreshed by executing the view queries when records are added, deleted, or otherwise modified.

SUMMARY

The described implementations relate to databases. One implementation can identify an active view that retrieves records from a database and determine one or more physical tables in the database that are referenced by the active view. The implementation can also track one or more columns in the one or more physical tables that are used by the active view and identify a change to the one or more physical tables in a transaction log of the database. When the change does not affect the one or more columns, the change can be treated as an ignorable change for the active view.

The above listed examples are intended to provide a quick reference to aid the reader and are not intended to define the scope of the concepts described herein.

BRIEF DESCRIPTION OF THE DRAWINGS

The accompanying drawings illustrate implementations of the concepts conveyed in the present patent. Features of the illustrated implementations can be more readily understood by reference to the following description taken in conjunction with the accompanying drawings. Like reference numbers in the various drawings are used wherever feasible to indicate like elements. Further, the left-most numeral of each reference number conveys the Figure and associated discussion where the reference number is first introduced.

FIGS. 6A and 6B show examples of user interfaces in accordance with some implementations of the present concepts.

DETAILED DESCRIPTION

Overview

This discussion relates to updating views in a database system. For example, in some implementations the views can be updated by tracking events in the database and rewriting view queries based on the tracked events. To provide an updated view, a view query can be rewritten to include identifiers of records that have changed over an interval of time, e.g., since the most recent prior execution of the view query. The rewritten view can retrieve only those records that have changed over the time interval. Thus, a user may be able to tell, based on the updated view, which records have changed since the last time the view was executed. The disclosed implementations can also be used to provide notifications when the output data of a view query changes.

The disclosed implementations are described in the context of a health care scenario. Providing efficient access to updated health care records can be a complex problem. For example, there may be many different sources of patient data, e.g., various hospitals, individual physicians, patient-supplied records, etc. Some of this data may be sensitive, e.g., a patient's status as an HIV-positive individual needs to be protected. Moreover, many different entities may need access to the records, such as doctors, medical billing personnel, various software applications, and/or the patients themselves. In some circumstances, near real-time updates need to be provided by the database, e.g., information about a patient may need to be provided to a MEDEVAC paramedic without any perceptible delay.

Health Care Scenario

Figure 1:
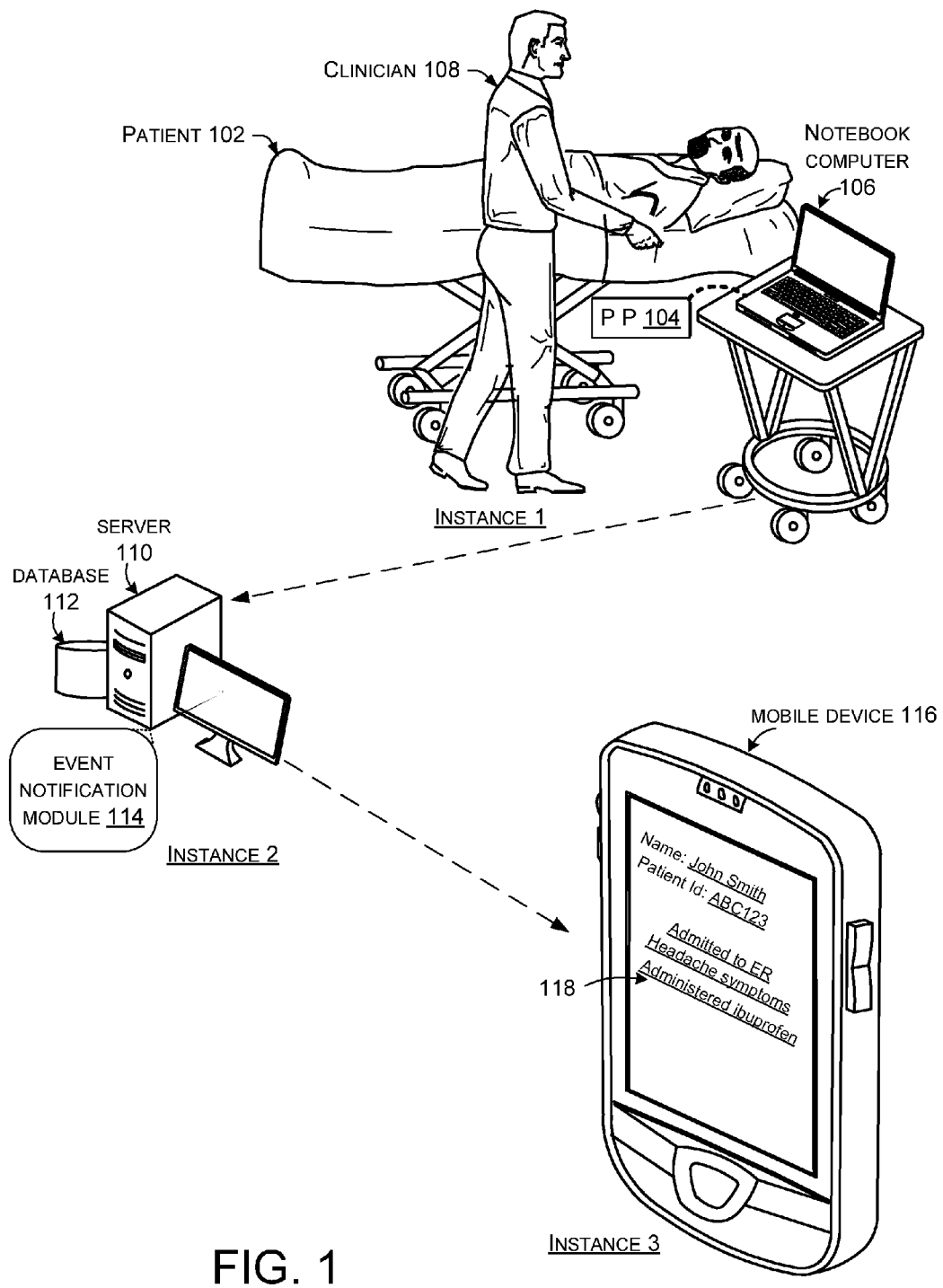
FIG. 1 shows an example scenario of providing a notification in accordance with some implementations of the present concepts.

FIG. 1 illustrates a scenario 100 in which data change tracking and event notification can be employed. Scenario 100 involves instances 1-3, each of which is discussed below. Starting at instance 1, example scenario 100 involves a patient 102 that presents for care at an emergency room. In this example, assume that patient 102 is triaged and that various patient parameters 104 are entered into the patient's file in notebook computer 106 by clinician 108. Notebook computer 106 can send updates to patient records stored at server 110 in database 112, shown at instance 2. For example, the updates can be based on the patient parameters entered when the patient is triaged. The patient parameters can include an indication of the patient's symptoms, e.g., headaches, and an administered treatment, e.g., ibuprofen.

In this example, patient 102 can be thought of as a patient of a general practitioner. The general practitioner can practice from an office that is located remotely from the emergency room, and can subscribe to receive updates when any current patients of the general practitioner are admitted to another facility for care. Scenario 100 generally illustrates how the general practitioner can be informed about their patient's emergency room visit, e.g., symptoms reported, treatments administered, etc.

For example, event notification module 114 of server 110 can determine that the general practitioner has subscribed to receive updates relating to this patient. Thus, the event notification module can send a notification to the general practitioner at their mobile device 116. Mobile device 116 can display a notification 118 that indicates the updated circumstances of the patient at instance 3.

In this case, event notification module 114 can notify the general practitioner using the various techniques discussed below. For example, the general practitioner can subscribe to receive event notifications based on changes to the records associated with their patients. The changes can cause one or more views to become out of date. Using the techniques discussed herein, out-of-date views can be filtered and rewritten so they retrieve only out-of-date records. Thus, in the example of scenario 1, the notification can be provided to the general practitioner by executing a view query that is rewritten to include a filter on a patient ID for patient 102. This can offer improved efficiency relative to, for example, executing a full view query that retrieves data for all of the general practitioner's patients and then using logic to determine which records retrieved by the full view query have changed.

Data Change Tracking

The following description will use certain database terminology that is described herein. For the purposes of this document, a base table is a table or view that is explicitly defined in the database schema for the database. Thus, a base table can represent either a view query that is defined in the schema, or a physical table in the database. A view query is a table constructed from the base tables by one or more relational operations, e.g., JOIN, SELECT, etc. A physical table is an underlying table in the database where records are physically stored and updated, and a view query or table is a table that is derived from the data in one or more physical tables. A target query is a view query that is associated with one or more notifications or events. Generally speaking, when an event such as a change to a physical table in the database would result in a change to the output of a particular target query, a corresponding notification can be generated for entities that are associated with the target query. One way for an entity to associate with a target query is via a subscription, discussed in more detail below. An active view is a target query that is currently associated with at least one entity that is subscribed to receive updates for that view.

A SQL DOM (structured query language domain object model) is a tree that describes the construction of a query from one or more base tables. A SQL DOM can include one or more classes that load a particular query by parsing a SQL statement. A SQL DOM can be used to rewrite a SQL statement to include one or more filter conditions, as set forth in more detail below. Note, however, that other suitable programming languages can also be used to implement the techniques disclosed herein. For instance, some of the concepts described herein can be implemented in the Java® programming language or using the .NET® framework.

Change data capture ("CDC") tables are tables that represent changes that have occurred to physical tables in a database. For example, CDC tables can show what data was included in a given record before and after each change. The CDC tables can also have timestamps, version numbers, or other fields associated with each change that can be used to determine whether a particular view or individual record is out-of-date. A CDC table is one example of a queryable transaction log of ongoing changes to a database, and is provided in SQL Server® database implementations. Another example of a queryable transaction log is a "redo" log in an Oracle® database implementation. In some implementations, queryable transaction logs are themselves implemented as database tables. As discussed in more detail below, using a queryable transaction log such as a CDC table to update views can be more efficient than recomputing the entire views directly from the underlying physical tables.

For the purposes of example, database 112 can include two tables—PATIENT and ADDRESS, having the following schema:

PATIENT: (PatientID, FirstName, LastName, Phone, AddressID)

ADDRESS: (AddressID, Street, Country, ZipCode)

Thus, PATIENT and ADDRESS are base tables in the database and can generally be represented as physical database tables in the database. These tables can be accessed by various view queries, e.g., a view query VQ1 having the following schema and query definition:

SELECT ZipCode FROM PATIENT p, ADDRESS a WHERE p.AddressID=a.AddressID

VQ1 provides, as output, a table with all zip codes with at least one patient.

VQ1 is constructed by taking the inner join of PATIENT and ADDRESS on the AddressID columns of these tables.

As another example, consider a view query VQ2:

SELECT PatientID, FirstName, Phone FROM PATIENT p, ADDRESS a WHERE p.AddressID=a.AddressID AND a.ZipCode='98065'

VQ2 provides, as output, the PatientID, FirstName, and Phone columns for those patients with the zip code 98065.

In some implementations, entities such as users or applications can request notifications on a given view query such as VQ1 or VQ2. For example, event notification module 114 can be configured to send a notification via an email or API (application programming interface) call whenever patient data changes for a patient living in zip code 98065. As mentioned above, those queries that are configured to provide such notifications are referred to as "target queries."

Note, however, that some target queries can be computationally expensive. If a target query changes frequently because of changes to the underlying database tables, this can result in many recomputations of the target query. However, note that not every change to the underlying database necessarily changes the output of every target query.

For example, VQ2 does not return the LastName column of the patient table, nor is VQ2 conditioned on this column. Thus, even assuming a user in the 98065 zip code changed their last name and a corresponding record was updated in the Patient table, VQ2 would still have the same output before and after the update. Thus, another computation of VQ2 does not necessarily need to be triggered by this particular change to the database. In other words, entities interested in VQ2 do not need to be updated because of the change to the LastName column. Generally speaking, the disclosed implementations can avoid recomputing target queries for each change to the underlying tables referenced by the target queries. Instead, the recomputations can be limited to instances when the updates to the underlying tables will actually result in different results for target queries.

Thus, some changes to the underlying records may not be relevant to any target query. For the purposes of this document, such a change is referred to herein as an "ignorable change." As another example, consider a change to the Street column of the ADDRESS table. Because this column is not referenced in VQ2, this is an ignorable change with respect to VQ2. Note, however, that changes to either (1) a column returned by a query or (2) a column used as a condition in the query can cause the query to need to be recomputed.

First Method Example

Figure 2:
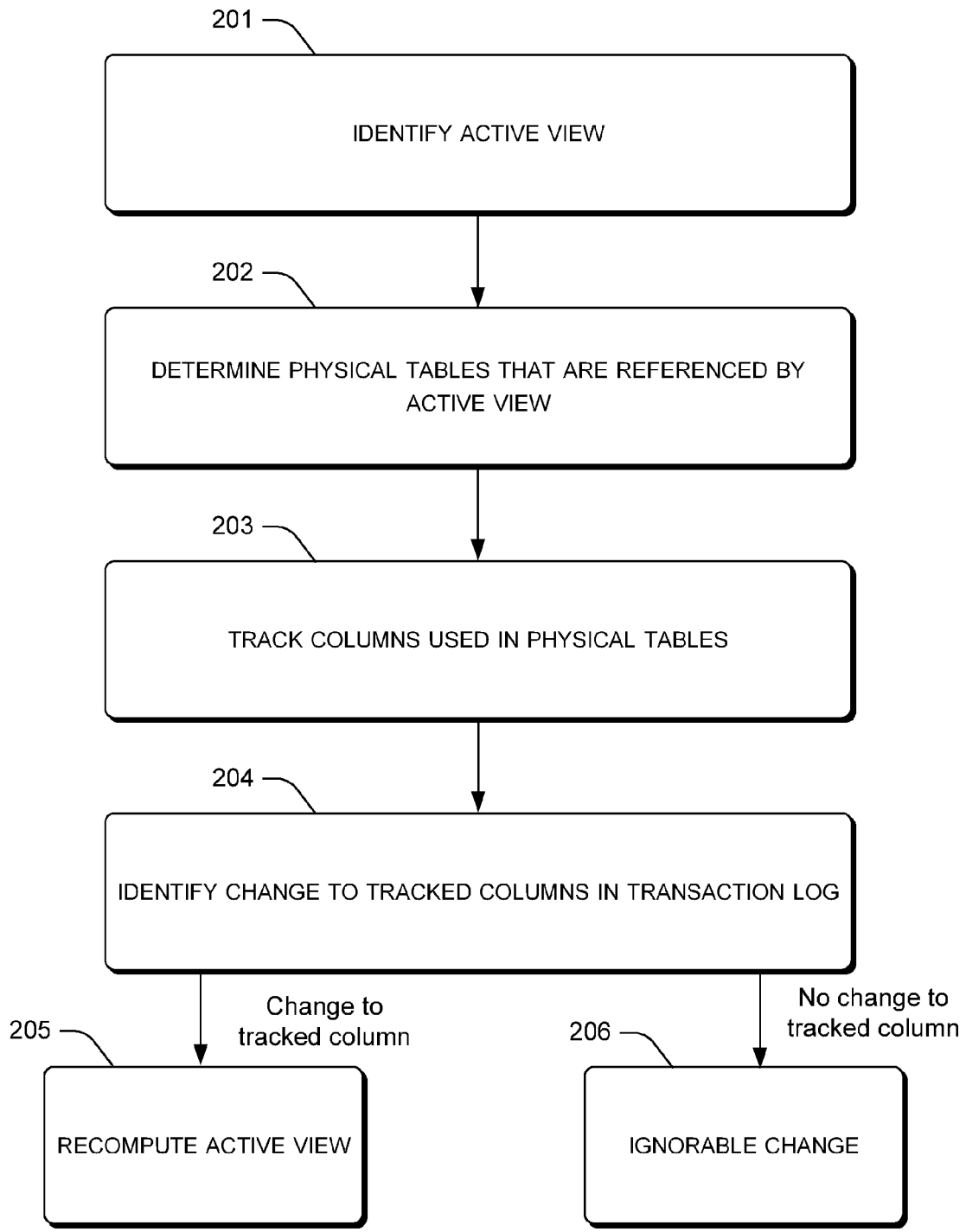
FIG. 2-5 show examples of flowcharts of methods in accordance with some implementations of the present concepts.

FIG. 2 illustrates an exemplary method that can be used to identify ignorable changes. For simplicity of exposition, the following example is discussed with respect to a single active view and a single change to a record in one table of the database. However, as discussed in more detail below, method 200 can be applied for any number of active views and for any number of changes to any number of tables in the database.

At block 201, an active view is identified. For example, from a list of currently active views, VQ2 can be identified as an active view. In some implementations, entities such as the general practitioner can subscribe to receive notifications of updates to the active view, as discussed in more detail below.

Next, at block 202, the physical database tables that are referenced by the active view can be determined. For example, VQ2 can be parsed to build a SQL DOM that references the physical tables that are accessed by VQ2. Note that, in some circumstances, this might involve recursively parsing base tables (SQL Views) until the SQL DOM contains only references to the underlying physical SQL Tables, as discussed in more detail below.

Next, at block 203, columns are tracked in the physical tables, e.g., the columns that are referenced in the active view. For example, as the physical tables are identified at block 202, event notification module 114 can also track the columns that are used in the projections, filters and join conditions of the active view.

Next, at block 204, a change to the tracked columns can be identified in a transaction log such as the aforementioned CDC tables. For example, event notification module 114 can query the transaction log to find changes for these columns of the SQL tables that are referenced by VQ2.

If there are changes to the tracked columns, method 200 moves to block 205, and the active view is recomputed by executing the view query again. Because there are changes to the columns of the physical tables that are referenced by VQ2, it follows that at least some of data retrieved by VQ2 has changed and VQ2 may be recomputed. For example, if new records are added to the PATIENT and ADDRESS tables for a patient with zip code 98065, VQ2 can be recomputed so that the new patient appears in the active view.

Otherwise, if there are no changes to the tracked columns, method 200 moves to block 206, and the change is treated as an ignorable change. As mentioned above, VQ2 does not need to be recomputed if the change in the transaction log is to the Street column of the ADDRESS table. Thus, from the perspective of VQ2, such a change is ignorable.

As mentioned above, method 200 can be performed on multiple views and multiple changes to multiple physical tables. In such implementations, method 200 can be used to identify changes that may be ignorable for all active views. Likewise, method 200 can be used to identify a subset of the active views that need to be recomputed, while identifying other active views that do not need to be recomputed.

Method for Retrieving Changed Records

For those changes that are not ignorable changes (ICs), those physical records that are actually affected by changes to the database can be retrieved to recompute one or more view queries. One way to do so is a "snapshot" approach by executing a view query of interest before and after one or more changes. The resulting outputs can be "diffed" or compared to see what view query outputs have changed as a result of the changes to the underlying database tables. For example, VQ2 could be executed before and after a change that adds a new patient with zip code 98065. The resulting two tables can be compared to identify the new record, and the general practitioner can be sent a notification about the new patient. However, it can be relatively inefficient to execute (1) the full view query for each change to the underlying database tables and (2) compare the resulting tables, particularly if the view query returns a large number of tables.

Figure 3:
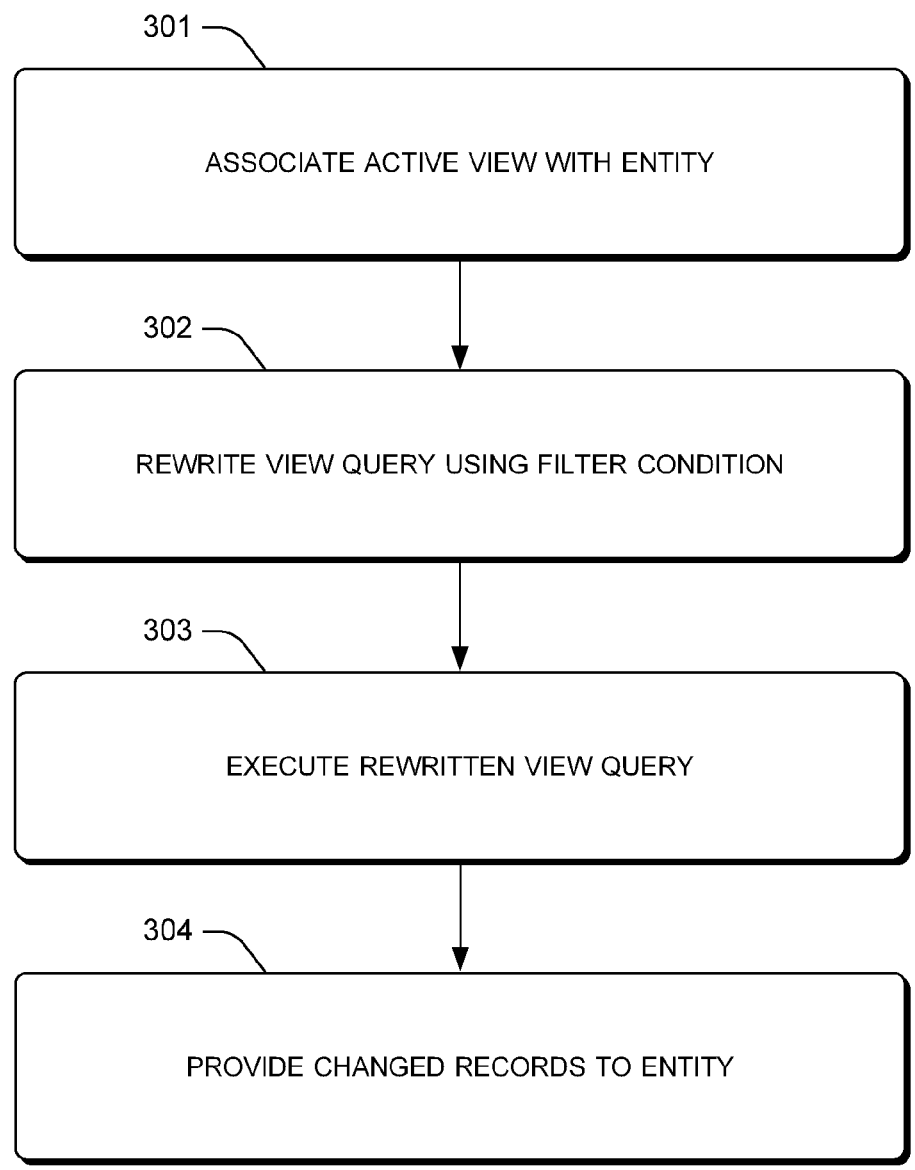

FIG. 3 illustrates an exemplary method 300 that can be used to update a view. The following implementation can leverage the transaction log to filter a view query so that the view query will return only those records that have changed as a result of the underlying changes to the database. Again, the following example is discussed with respect to a single active view and a single change to a record in one table of the database. However, as discussed in more detail below, method 300 can be applied for any number of active views and for any number of changes to any number of tables in the database.

At block 301, an active view is associated with an entity such as a user or an application. For example, a user can use a graphical user interface to choose one or more views to monitor, or an application can programmatically select one or more views to monitor. When the entity decides to monitor a particular view, the entity can subscribe to receive a notification when any data changes on that view. A corresponding event definition can be created that associates the entity with the view. For example, the event definition can indicate that the general practitioner should be notified any time a new patient is added in zip code 98065, is admitted to the emergency room, is administered a drug, etc.

Next, at block 302, view queries can be rewritten using a filter condition. For example, the transaction log can be accessed to determine which records have changed over a given time interval, e.g., since the last time the entity was notified of a change in the view, the last time the view query was executed, etc. The view query can be parsed and a SQL DOM can be built that references only the physical tables in the database using one or more of the filter conditions. For example, the filter conditions can include primary keys extracted from the transaction log for records that have changed.

The following specific example is discussed in more detail below. In specific implementations where a CDC table is being used as the transaction log, a query such as:
    SELECT*FROM Patients
can be rewritten as:
    SELECT*FROM (select*from Patients WHERE PatientId IN ({Primary Keys in CDC}))
where the filter condition is specified in the rewritten view query via the underlined portions shown above. Note, however, that the filter condition identified above is specific to CDC implementations. More generally, the filter condition can be represented in any way that identifies the changed rows in the physical tables. For example, in Oracle® implementations, primary keys extracted from the redo log can be used as the filter condition in the rewritten query.

Next, at block 303, the rewritten view query can be executed. Because the rewritten view query includes the filter conditions from the transaction log, the rewritten view query will return only those records that have changed since the previous execution of the view query.

Next, at block 304, the changed records are provided to the entity. In some implementations, method 300 is implemented as a background service that periodically rewrites each active view based on the transaction log. The rewritten views can also be periodically executed by the background service. Thus, method 300 can be used to continuously identify relevant events for entities and provide updated results to those entities. In some implementations, entities can specify how often individual views are recomputed, e.g., in terms of a time interval or frequency.

Note, however, that method 300 does not need to be performed periodically. Rather, in some implementations, method 300 can be initiated each time a database record update is received, or using other criteria to trigger the method. In such implementations, method 300 can be initiated responsive to predefined conditions including, but not limited to, identification of at least one non-ignorable change.

Note also that the keys used for the filter conditions of the rewritten queries can be taken from the transaction log instead of directly from the underlying physical tables. This can be more efficient than using the underlying physical tables, because over a given time interval of interest there may be relatively few changed records in the transaction log, e.g., many fewer records than in the complete physical tables. Moreover, consider using method 300 in the context of a view query that is built on several other view queries instead of directly on the underlying physical tables. Because the filter conditions are specified in the top-level view query, the filter conditions can be recursively filtered down through the lower-level view queries until a SQL statement referencing only the physical tables is generated. More generally, each view query can be associated with one or more intermediate view queries that collectively obtain data from one or more physical tables. Note also that some implementations use an external process to monitor changes to the physical database tables and the output of this external process can include the primary keys of the changed records.

Specific Examples of Rewritten Queries

Examples of how some of the queries can be rewritten using method 300 are shown below using a pseudocode notation based on SQL. The following code examples are particular to SQL Server® implementations and accordingly the rewritten queries shown below reference CDC tables in the filter conditions. The following examples can be extended to other implementations by rewriting the filter conditions to refer to the appropriate transaction log, e.g., a redo log in Oracle®, etc. Note that the approach discussed above for identifying changed records can be leveraged to identify changes to records that currently meet the query criteria. For view queries that select records from multiple physical tables, one general approach is as follows. For physical tables A, B, and C let deltaA represent changes in the CDC tables to table A, deltaB represent changes to table B, and deltaC represent changes to table C. A union operation can be used to combine the changes for one table with the other tables, e.g., following the pattern "deltaA+b+c, a+deltaB+c, a+b+deltaC," and so on for more tables.

(1) Single Table and no WHERE Clause: Consider a view query that returns all rows (no WHERE clause) and all columns from the Patients table:

SELECT*FROM Patients

This query can be rewritten using information from the CDC tables to return the query rows that are affected by changes to the underlying tables, without returning query rows that have not been affected by the changes to the underlying queries. This can be accomplished by adding an additional filter on the primary key of the Patients table, e.g., PatientId, as follows:

SELECT*FROM (select*from Patients WHERE PatientId IN ({Primary Keys in CDC}))

By including the primary keys from the changed records in the query condition "WHERE PatientId IN ({Primary Keys in CDC})," the changes to the view query can be identified. Note that this approach can result in fewer data accesses (e.g., reads) than would be required to execute the view query before it was rewritten with the primary keys from the CDC tables.

(2) Single Table with WHERE Clause: Now, consider a query that returns the Patients living in particular ZipCode using WHERE clause.

SELECT*FROM Patients WHERE ZipCode='98065'

This query can be rewritten in the manner discussed above, e.g., using information from the CDC tables to return the affected query rows by adding an additional filter on primary keys using CDC tables as follows:

SELECT*FROM (select*from Patients PatientID IN ({Primary Keys in CDC} as Patients) WHERE ZipCode='98065'

(3) Multiple Tables with INNER JOIN: Now, consider a query that uses an Inner Join operation to retrieve information from two tables and filters the patients using ZipCode:

SELECT*FROM Patients p, Visits v WHERE p.PatientId=v.PatientId AND p.ZipCode='98065'

This query can be rewritten in the manner discussed above, e.g., using information from the CDC tables to return the affected query rows by adding an additional filter on primary keys using CDC tables. In this example, the query is rewritten using a primary key filter for each table and then a UNION is used to obtain the complete table:

SELECT*FROM (Select*from
　Patients WHERE PatientId IN (Primary Keys in Patients CDC)) p,
　Visits v WHERE p.PatientId=v.PatientId AND p.ZipCode='98065'
UNION
SELECT*FROM Patients p, (Select*from
　Visits WHERE VisitId in {Primary Keys in Visits CDC}) v WHERE p.PatientId=v.PatientId AND p.ZipCode='98065'

(4) Using LEFT OUTER JOIN: Now, consider a query that uses a LEFT OUTER JOIN operation to get all patients' information and their addresses, if any:

SELECT*FROM Patient p LEFT OUTER JOIN Address addr ON p.PatientID=addr.PatientID Queries using LEFT and/or RIGHT OUTER JOINS can be re-written such that the entire table of the non-filtered table is not included, but the filter column is not eliminated. For example, if the table on the receiving side of a left/right outer join is not affected by the set of primary keys or the table filters, then the table can be eliminated to improve performance when determining which rows changed:

SELECT*FROM (Select*from Patient (PatientId IN ({Primary Keys in Patient CDC})) p
LEFT OUTER JOIN Address addr ON p.PatientID=addr.PatientID
UNION
SELECT*FROM Patient p INNER JOIN {Select*from Address
WHERE AddressID in (Primary Keys in Address CDC}))

(5) Using RIGHT OUTER JOIN: Now, consider a query with multiple RIGHT OUTER JOIN operations:

SELECT*FROM Patient p RIGHT OUTER JOIN Address addr
ON p.PatientID=addr.PatientID
RIGHT OUTER JOIN Detail d ON d.PatientID=addr.PatientID The RIGHT JOIN after the target table being filtered ("Patient") can be converted into Inner Joins as follows:

SELECT*FROM (Select*from Patient (PatientId IN ({Primary Keys in Patient CDC})) p
INNER JOIN Address addr ON p.PatientID=addr.PatientID
INNER JOIN Detail d ON d.PatientID=addr.PatientID
UNION
SELECT*FROM Patient p
RIGHT OUTER JOIN (select*from Address (PatientId IN ({Primary Keys in Address CDC})) addr ON p.PatientID=addr.PatientID
INNER JOIN Detail d ON d.PatientID=addr.PatientID
UNION
SELECT*FROM Patient p RIGHT OUTER JOIN Address addr ON p.PatientID=addr.PatientID
RIGHT OUTER JOIN (select*from Detail (PatientId IN ({Primary Keys in Detail CDC})) d ON d.PatientID=addr.PatientID (6) Full Join: For a FULL JOIN, the query can be rewritten as a combination of LEFT JOIN and RIGHT JOIN operations. If the target table is on the left side of the JOIN condition, the query can be converted into a LEFT JOIN. If the target table is on the right side of the JOIN condition, the query can be converted into a RIGHT JOIN. Any additional FULL JOIN after the target table can be converted into a LEFT JOIN.

(7) Correlated Sub-Queries #1: The following example shows a sub-query that retrieves product information for which the product model is a 'blood pressure monitor,' where the ProductModelID numbers match between the Product and ProductModel tables.

SELECT*FROM Product p WHERE EXISTS
(SELECT*FROM ProductModel pm WHERE p.ProductModelID=pm.ProductModelID
AND pm.Name=blood pressure monitor)

This query can be rewritten using information from CDC tables to return the affected query rows:

SELECT*FROM (Select*from Product
WHERE ProductID IN ({Primary Keys in Product CDC})) p WHERE EXISTS
(SELECT*FROM ProductModel pm WHERE p.ProductModelID=pm.ProductModelID
AND pm.Name='blood pressure monitor')
UNION
SELECT*FROM Product p WHERE EXISTS
(SELECT*FROM (Select*from ProductModel
WHERE ProductModelID IN (Primary Keys in ProductModel CDC})) pm WHERE p.ProductModelID=pm.ProductModelID
AND pm.Name='blood pressure monitor')

(8) Correlated Sub-Queries #2: The following example uses two correlated sub-queries to find the names of employees who have sold a particular product:

SELECT DISTINCT c.LastName, c.FirstName FROM Person.Contact c
JOIN HumanResources.Employee e ON e.ContactID=c.ContactID WHERE EmployeeID IN
(
SELECT SalesPersonID FROM
Sales.SalesOrderHeader WHERE SalesOrderID IN
(
SELECT SalesOrderID
FROM Sales. SalesOrderDetail
WHERE ProductID IN
(
SELECT ProductID FROM Production. Product p
WHERE ProductNumber='BK-M68B-42')
)
)

This rewritten query is provided in a manner similar to that discussed above with respect to the RIGHT OUTER JOIN of example 5.

(9) Using UNION ALL Clause #1: The following examples uses a UNION ALL clause to retrieve and combine records from multiple tables.

SELECT*FROM ProductA
UNION ALL
SELECT*FROM ProductB

The above query can be re-written as follows to get changed records using information from CDC tables, e.g., if both tables are affected:

SELECT*FROM (Select*from ProductA WHERE ProductID IN ({Primary Keys in ProductA CDC})
UNION ALL
SELECT*FROM (Select*from ProductB WHERE ProductID IN ({Primary Keys in ProductB CDC})

(10) Using UNION ALL Clause #2:
SELECT*FROM ProductA
UNION ALL
SELECT*FROM ProductB The above query can be re-written as follows to get changed records using information from CDC tables, e.g., if only one table is changed:

SELECT*FROM (Select*from ProductA WHERE ProductID IN ({Primary Keys in ProductA CDC})
UNION ALL
SELECT*FROM (Select*from ProductB WHERE 1=2)

Note that the above technique may only find records where the current values of data in the query meet the query criteria and are different from the previous values of data returned by that query. If, however, there are multiple changes to a record between 2 intervals, this approach may not identify those records that change back to their previous values. For example, if a value X goes from 1 to 10 and back to 1 within a specific interval and a view query is used to identify changed records where X>5, the above rewritten queries may not identify this change.

This can be problematic in some situations, e.g., if the general practitioner wishes to be notified when a patient's blood pressure is out of the normal range, the general practitioner may not be notified if the patient's blood pressure goes from normal to out of range and back to normal before the view query is updated. In other words, before the view query is updated, the patient's blood pressure would return to normal and no change would be identified, and thus the general practitioner would be unaware that the patient's blood pressure had actually gone outside the normal range at some point in time. The following "complete history" queries are examples of how the above-identified examples can be rewritten to capture changed data under such circumstances.

(1) Single Table and no WHERE Clause:
SELECT*FROM (select*from CDCPatients)

(2) Single Table with WHERE Clause:
SELECT*FROM (select*from CDCPatients as Patients) WHERE ZipCode='98065'

(3) Multiple Tables with INNER JOIN:
SELECT*FROM (Select*from CDCPatients p, (select*Visits UNION CDC Visits) v
WHERE p.PatientId=v.PatientId AND p.ZipCode='98065'
UNION
SELECT*FROM (select*Patients UNION CDCPatients) p, (Select*from CDC Visits) v
WHERE p.PatientId=v.PatientId AND p.ZipCode='98065'

(4) Using LEFT OUTER JOIN:
SELECT*FROM (Select*from CDCPatient) p LEFT OUTER JOIN
(select*Address UNION CDCAddress) addr ON p.PatientID=addr.PatientID
UNION
SELECT*FROM (select*Patient UNION CDCPatient) p INNER JOIN (Select*from CDCAddress)

(5) Multiple RIGHT OUTER JOIN:
SELECT*FROM (Select*from CDCPatient) p

INNER JOIN (Select*from Address UNION CDCAddress) addr ON p.PatientID=addr.PatientID
INNER JOIN (Select*from Detail UNION CDCDetail) d ON d.PatientID=addr.PatientID
UNION
SELECT*FROM (Select*from Patient UNION CDCPatient) p
RIGHT OUTER JOIN (select*from CDCAddress) addr ON p.PatientID=addr.PatientID
INNER JOIN (select*from Detail UNION CDCDetail) d ON d.PatientID=addr.PatientID
UNION
SELECT*FROM (select*from Patient UNION CDCPatient) p
RIGHT OUTER JOIN Address addr ON p.PatientID=addr.PatientID
RIGHT OUTER JOIN (select*from CDCDetail) d ON d.PatientID=addr.PatientID (6) For FULL JOIN: A FULL JOIN can be rewritten with RIGHT and LEFT JOIN(s). The RIGHT JOINS can include the rows from the CDC table rewrite. For example:
SELECT*FROM Patient p FULL JOIN
Addr ON p.PatientID=addr.PatientID
can be rewritten:
SELECT*FROM (Select*from CDCPatient) p LEFT OUTER JOIN
(select*Address UNION CDCAddress) addr ON p.PatientID=addr.PatientID
UNION
SELECT*FROM (select*Patient UNION CDCPatient) p RIGHT JOIN (Select*from CDCAddress) addr ON p.PatientID=addr.PatientID (7) Correlated Sub-Queries #1:
SELECT*FROM (Select*from CDCProduct) p WHERE EXISTS
(SELECT*FROM (select*ProductModel UNION CDCProductModel) pm
WHERE p.ProductModelID=pm.ProductModelID
AND pm.Name='blood pressure monitor')
UNION
SELECT*FROM (select*Product UNION CDCProduct) p WHERE EXISTS
(SELECT*FROM (Select*from CDCProductModel) pm
WHERE p.ProductModelID=pm.ProductModelID
AND pm.Name='blood pressure monitor')

(8) Correlated Sub-Queries #2: Again, this can be handled similar to query described in point #5.

(9) Using UNION ALL Clause #1:
SELECT*FROM (Select*from CDCProductA)
UNION ALL
SELECT*FROM (Select*from CDCProductB)

(10) Using UNION ALL Clause #2:
SELECT*FROM (Select*from CDCProductA)
UNION ALL
SELECT*FROM (Select*from CDCProductB)

View Materialization

The above implementations can also be used in the context of view materialization. Materialized views can be created by periodically executing view queries and caching the results. This can be useful under circumstances where views are accessed with relatively high frequency, because view requests can be serviced using the materialized tables without having to execute the view query for each incoming request. However, under some circumstances, the added efficiencies provided by using materialized views are not enough. For example, consider environments where real-time or near-real time data availability is desirable (e.g., a hospital environment or financial institution). Periodic execution of view queries under these circumstances necessarily means that there are times when the materialized views are out of date.

Techniques similar to those described above with respect to view queries can also be used to provide updated materialized views. For example, as discussed above, the transaction log can be leveraged to selectively update materialized views. Such implementations can offer improved efficiencies for maintaining materialized views, because the full view query does not need to be re-executed each time the materialized view is updated.

Figure 4:
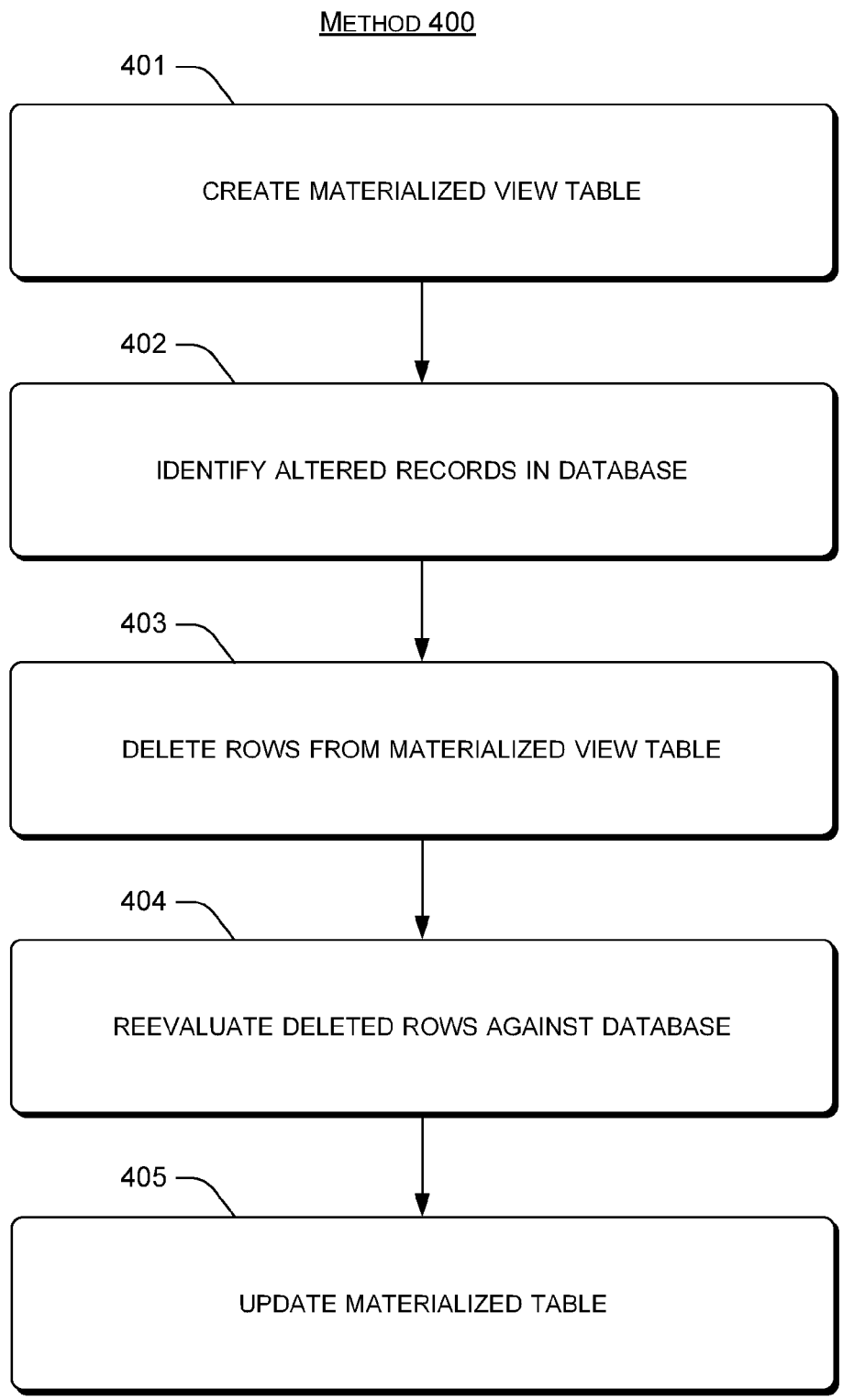

FIG. 4 illustrates an exemplary method 400 for maintaining a materialized view table. Again, the following example is discussed with a relatively simple example, e.g., a single materialized view and a single change to a record in one physical table of the database. However, as discussed in more detail below, method 400 can be applied for any number of materialized views and for any number of changes to any number of tables in the database.

A materialized view table is created at block 401. For example, for a given view query, a corresponding empty table can be created. In some implementations, the table can initialized by executing the view query a first time to populate the materialized view table.

Next, altered records in the database can be identified at block 402. For example, as discussed above with respect to methods 200 and 300, a transaction log such as the CDC tables can be used to determine what changes have happened to individual records in the physical database tables. In some implementations, the altered records in the transaction log are associated with corresponding messages in a message pipeline. Using temporal metadata associated with the messages, altered records for a particular interval of time can be identified. This can limit the number of altered records that are applicable to any given update of a materialized view. Note also that, to further enhance efficiency, block 402 can be performed only for changes that are not ignorable changes from the perspective of the view query.

Next, rows can be deleted from the materialized view table at block 403. For example, for each altered row ID (e.g., a primary key for a record) in the materialized view table, the entire row can be deleted.

Next, the deleted rows can be reevaluated against the database at block 404. For example, the view query can be rewritten as discussed above using the row IDs of the altered records. Thus, the results of the executed view query will be limited to the records that have been updated since the last time the view query was executed. Accordingly, only the deleted rows are retrieved by the rewritten view query.

Next, the materialized view table is updated at block 405. For example, the records retrieved at block 404 can be inserted into the materialized view table for the deleted row ID's. Accordingly, the materialized view table is now up to date with respect to the altered records identified at block 402.

Note that the operations discussed above with respect to deleting and inserting rows of the materialized view table can equivalently be performed by overwriting these rows with the data retrieved at block 404, without necessarily deleting these rows from the materialized view table. In other words, method 400 can be performed, e.g., using SQL UPDATE statements instead of using DELETE/INSERT statements, etc. More generally, the current state of the materialized view table can be updated using any acceptable technique to modify the contents of the materialized view table, including, but not limited to, insertions, deletions, updates, merges, etc.

Note also that, in some implementations, applications may query against the materialized table directly instead of against the physical tables or other views. Thus, view queries against materialized view tables can use operations such as "SELECT*" from the materialized view table. Also note that method 400 can be performed periodically to update the materialized view table. In some implementations, near real-time updates can be achieved by setting the update period to relatively short durations, e.g., on the order of 10 milliseconds. Method 400 can also be initiated responsive to detecting any database event that would cause a materialized view table to be out of date. This can reduce latency even further and can provide real-time levels of performance.

In still further implementations, the frequency with which a given materialized view is updated can depend on the relative importance of having up-to-date data in the table. For example, in an operating room or MEDEVAC scenario, a health care professional may need to know with complete certainty that certain patient information is not stale. In such implementations, 10 millisecond refresh intervals for the materialized view table might be reasonable. For a general practitioner scheduling regular office visits for patients, overnight updates may be sufficient to keep a reasonably up-to-date schedule.

As an example of how the above discussion can be employed in scenario 100, mobile device 116 can include an application that queries against one or more materialized tables in database 112. The application can be configured to retrieve and format columns from the materialized tables in a user-friendly fashion. For example, the application can list the retrieved information in an order such as (1) whether the patient is presently admitted for treatment, (2) the patient's symptoms, and (3) any treatments administered to the patient, as shown in notification 118.

In scenario 100, the message pipeline can include messages sent from notebook computer 106 to database 112, as well as various other devices that can update database 112, e.g., other hospitals, insurance companies, etc. In some implementations, each message in the pipeline is given a sequentially-increasing message ID. These message ID's can serve as temporal metadata because, as between any two messages, the message with the higher message ID was received by database 112 later than the message with the lower message ID.

Each message can cause changes to the physical database tables. In some implementations, any message ID that alters a physical database table results in a new sequential Row ID. Thus, for any interval of interest, the records that were altered during that interval can be identified using the message ID's and/or the row ID's. Note also that timestamps can also be used in addition to, or in place of, the sequential message and row ID's.

Using the techniques described above with respect to method 400, the messages in the message pipeline can be used to define which primary keys are extracted from the transaction log and used as filter conditions on the rewritten queries. Thus, the messages in the pipeline constrain which primary keys are used for each update to a given materialized view. Because this can mean that relatively few records may need to be updated, it is possible to provide a low-latency solution via the materialized view tables.

Event Subscriptions

The above implementations can provide efficient techniques for providing updated data to various users. In some cases, many different users are constantly receiving different data streams to update different views of the underlying records. As mentioned above, users can be notified when particular views of interest are updated.

However, it is not always feasible for users to register to be notified in every conceivable instance that would be of interest to the user. For example, assume the general practitioner wishes to register for notifications whenever one of their patients is prescribed any medication from a class of medications, e.g., non-steroidal anti-inflammatory drugs or NSAIDS. There may be hundreds of different drugs in this particular class. It would be relatively burdensome to require the physician to request an individual notification for each and every NSAID drug. Moreover, in the event a new NSAID drug was approved for use by a regulatory agency, the physician may not even be aware that the newly-approved drug is available and therefore may not realize that he/she needs to add a new notification on this drug.

The following implementations can facilitate providing users with subscription mechanisms to obtain data of interest without having to register notifications with such particularity. For example, users can register subscriptions such that they are notified when data falls within a particular range, when correlated events occur, when certain events do not occur, etc. Users can also subscribe to be notified of changes in the data that relate to certain concepts, e.g., the aforementioned physician could register to be notified based on a predefined concept such as "NSAID drugs," etc. Users can also subscribe via free-form keywords, e.g., in instances when there is not a suitable predefined concept available.

Figure 5:
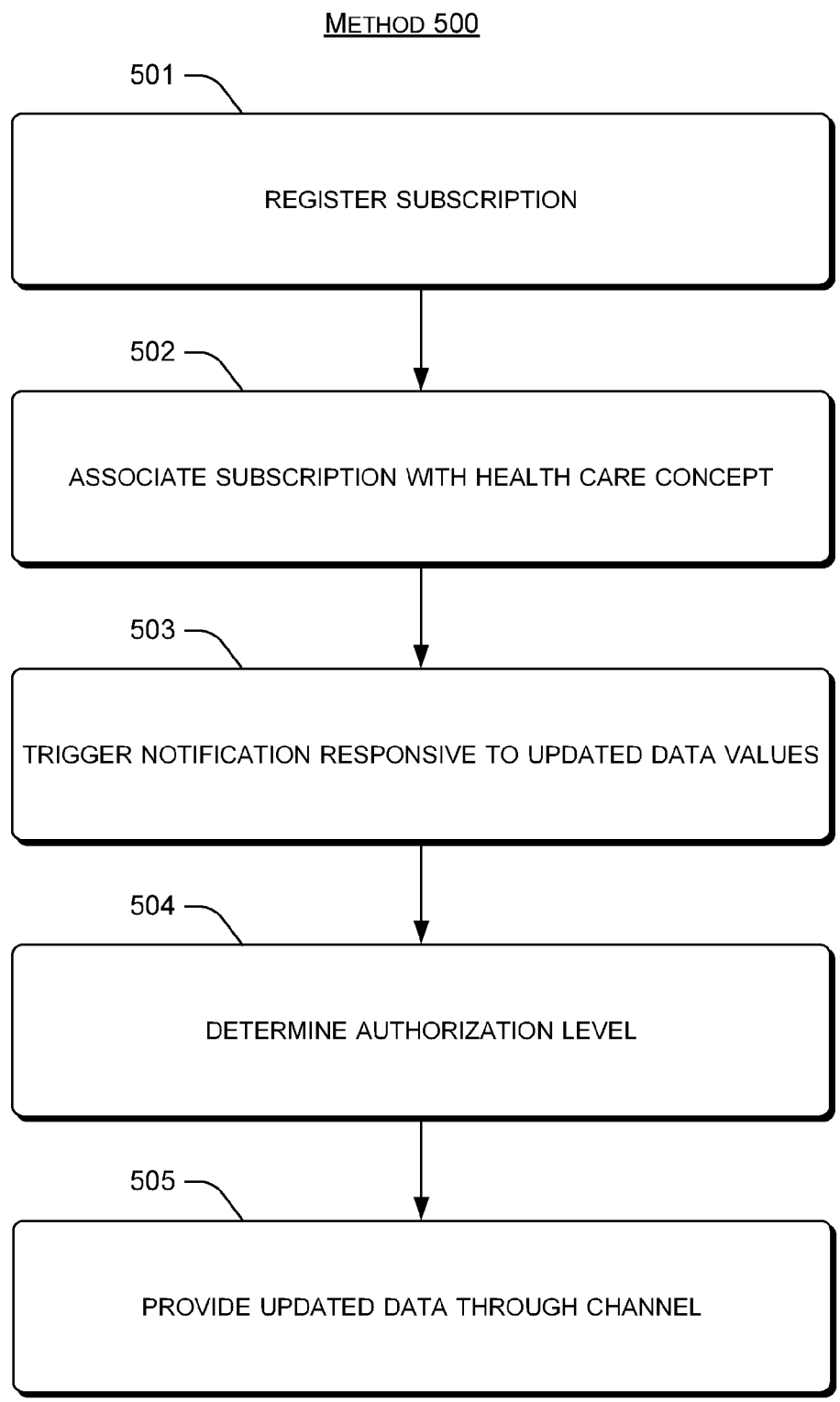

FIG. 5 illustrates an exemplary method that can be used to notify a user that has registered a subscription. The following discussion with respect to FIG. 5 is general in nature. More specific implementations follow that identify details of how different types of subscriptions can be implemented consistently with method 500. In the following example, database 112 is a health care database that includes one or more personal health care records such as an individual patient record for patient 102.

At block 501, an entity can register a subscription. For example, the entity could be a user such as the aforementioned general practitioner, a nurse, a group of individuals, or a non-human entity such as an application. The subscription can be stored in association with the entity.

Next, at block 502, the subscription is associated with a health care concept. Generally speaking, this can involve storing identifiers in association with the subscription, such as one or more identifiers of data for which the entity would like to receive notifications. For example, in the example of the physician mentioned above, the identifier "NSAID drugs" could be stored in association with the physician's subscription. As discussed in more detail below, the subscription can be used to notify the entity when data in a personal health care record is updated in a health care database. Thus, the identifier can relate to a health care concept, in this case, "NSAID drugs." Note that the identifier "NSAID drugs" can be viewed as a contextual identifier corresponding to a multitude of different drugs in the NSAID class. In some implementations, the identifier can be expanded, e.g., to a list of each of the different NSAID drugs (e.g., aspirin, ibuprofen, etc), and each individual drug can be associated with the subscription.

Next, at block 503, a notification can be triggered responsive to an updated data value. For example, if a personal health care record is updated by a change to a physical table or view in the database such that the personal health care record includes one of the drugs on the list, a notification can be triggered. Note that the notification can be triggered without directly accessing the physical database tables. Instead, the transaction log can be used to detect the updated data value and trigger the notification. Furthermore, in some implementations, the updated data is not yet persisted in the database when the notification is triggered. Instead, for example, a software method that updates the database (e.g., via embedded SQL, etc.) can be configured with logic to trigger the notification before updating the database, e.g., by checking for a value or particular range of values before the database is updated.

Next, at block 504, an authorization level for the entity can be determined. For example, a physician may have access to see all drugs taken by any of their patients. However, this information may not be available to other individuals, e.g., medical billing personnel, etc.

Next, at block 505, updated data relating to the personal health record is provided to the entity by sending the notification via an appropriate channel, provided the entity is authorized. For example, drugs used by patients may be considered sensitive data. Accordingly, it may be inappropriate to send information that a patient has started using aspirin via an unsecure channel such as an unencrypted text message. Instead, for example, this information could be provided via a more secure channel, such as an encrypted email. In contrast, for example, information about a patient rescheduling an appointment could be appropriate for providing to the general practitioner via less secure channels such as the aforementioned text message.

In some implementations, method 500 can be viewed as allowing the entity to register a context-sensitive subscription that allows the entity to use predefined notification concepts such as the aforementioned predefined mappings of drug classes to individual drugs. Method 500 can also be implemented using free-form notification concepts. For example, the general practitioner could provide one or more keywords at block 501 that are used at block 502 to determine the associated data values. As a specific example, even if there is no predefined mapping from "NSAID" to "ibuprofen," it is still likely that a keyword search on "NSAID" would return search results with the term "ibuprofen." Conceptual notification schemes using keywords can be implemented by using the keyword to search a corpus of documents and identifying related terms, e.g., the keyword "NSAID" may return the related terms "ibuprofen," "aspirin," etc. In such implementations, the general practitioner can be alerted when updates to the database include the related terms but do not necessarily include the keyword itself.

In still further implementations, block 501 can allow the entity to register a subscription that references a defined range of values. For example, the defined range could be a total cholesterol measurement for a patient. Note that the range does not necessarily need to be defined on columns that are present in the physical database tables. For example, the total cholesterol value may not be represented in the physical database tables, but instead could be determined by a view query that sums together two physical columns in the database, e.g., low-density lipoprotein (LDL) and high-density lipoprotein (HDL) columns.

Method 500 can also leverage codified medical data in some implementations. For example, the physical records in the database may include a predefined code for the drug "ibuprofen." Block 502 of method 500 can associate the general practitioner's subscription request for "ibuprofen" with the predefined code. This is another example of how notification can be accomplished even in circumstances where the underlying physical records do not include the concepts of interest to the subscribing entity. As another example, synonymous terms can be mapped at block 502, so, for example, an entity registering to receive a notification on a medication such as "ibuprofen" can receive a notification on a corresponding brand name, e.g., Motrin®. Note that the opposite is also true, e.g., the entity could register a subscription for the brand name and receive notifications when the generic drug name appears in one or more records.

As another example, the subscription mechanisms presented herein can be used to correlate multiple events. The correlated events do not necessarily need any predefined relationship in the underlying physical records and/or any view queries. For example, the general practitioner could register to receive a notification on the concepts "ibuprofen" and "pain" any time these two concepts are reflected in updates to the database within a predefined time interval, e.g., one day. The concept "ibuprofen" could be expanded or mapped to a brand name as mentioned above, and the concept "pain" could be mapped to a "headache." Thus, the physical database records could be updated with the values "Motrin®" and "headache" within 24 hours for a particular patient. The general practitioner would receive a corresponding notification, e.g., as shown in scenario 100, even though the general practitioner did not explicitly identify Motrin® and/or headaches as concepts of interest. This approach can be applied to other types of medical data, e.g., lab results, family histories, surgeries, occurrence or non-occurrence of events such as taking medication, etc.

In still further implementations, statistical techniques can be used to determine notification concepts that can be used to implement subscriptions for different entities. For example, certain values in the physical records or derived values in the views may tend to be statistically correlated. In other words, the drug acetaminophen is not considered an NSAID. However, acetaminophen can be used in many clinical contexts where an NSAID such as aspirin or ibuprofen would also be appropriate. In some implementations, subscribers may be able to subscribe for notifications on closely-related concepts. For example, a subscribing entity that requests notifications on "NSAIDs" could be given an option to also receive notifications on statistically-related concepts. In scenario 100, if the general practitioner has selected this option, the general practitioner may receive a notification when the patient receives acetaminophen even though the concept that they specified, NSAIDs, does not strictly include acetaminophen. In contrast, had the general practitioner not selected this option, then they would not be notified if the patient were to receive acetaminophen because the notifications would be strictly limited to instances where NSAIDs were used.

Note that method 500 can be integrated with methods 200, 300, and/or 400 described above. For example, ignorable changes can be identified not only for individual view queries, but also for conceptual notification schemes that are not directly reflected by any particular view query. As but one example, in the NSAID scenario discussed above, there may be a first view query that selects patient records on all NSAID medications by an expanded list of all known NSAID drugs. There may be a second view query that selects patient records that include the term acetaminophen. From the perspective of this subscription, an ignorable change is a change that is ignorable for both of these view queries. However, if the change necessitates recalculating either of these two view queries, an appropriate notification can be generated using a rewritten view query. Likewise, note that the notification can, in some implementations, be generated by querying the materialized view tables instead of the physical tables.

From some perspectives, the keys used for the rewritten view queries mentioned above can be viewed as context-based keys. For example, the transaction log can be searched for changes that meet criteria defined by the subscription, e.g., data within a particular range, data that is synonymous with a subscribed concept, etc. The primary keys selected from the records in the transaction log are therefore selected based on context that is defined at least partly by the subscription.

In some implementations, notifications provided, e.g., by block 505 of method 500 are context-aware. One example is mentioned above with respect to using encrypted email for providing confidential information such as what drugs a patient may be taking. More generally, different subscribers can have different roles with different permissions. For example, the roles of "physician," "nurse, and "billing personnel" can have progressively decreasing permissions. Entities with the role of physician can have access to all medical data for their patients, e.g., lab results, symptom information, etc. Nurses may not have access to lab results but may have access to symptom information. Billing personnel may not have access to either, and may only have access to information such as codes for procedures performed, insurance information, etc.

In further implementations, relationships between a triggering entity and a receiving entity can be used to refine which data is provided to a particular entity. As mentioned above, the general practitioner (receiving entity) can receive updates when their own patients (triggering entity) check into the emergency room, but not necessarily for all patients who happen to check into the emergency room. In some implementations, different priorities are defined for different users. As suggested above, the frequency of updates provided to a MEDEVAC paramedic may be far more frequent than the frequency of updates provided to a general practitioner, for reasons related to the relative urgency associated with these differing roles. Note also that active or materialized views associated with a high-priority entity can be updated more frequently than active or materialized views associated with a lower-priority entity.

In some implementations, delivery channels with relatively low latency can be used to deliver messages to higher-priority recipients, while delivery channels with relatively high latency can be used to deliver messages to lower-priority recipients. A cardiac surgeon performing surgery on a patient the same day could be a higher priority recipient of an event notification compared to the patient's general practitioner. This could mean that the general practitioner gets an e-mail report at the end of the week, while the surgeon could receive a short message service ("SMS") message, a page, an e-mail, and a custom notification in an inbox that is associated with the health care database. Additionally, the surgeon's operating room assistants can also be notified by relatively low-latency channels such as the aforementioned SMS message.

As also mentioned above, different delivery channels may be more appropriate for different types of information. For example, some information such as HIV status may be categorically prohibited from being communicated via unencrypted communications. Other, less sensitive information such as patient appointments can be provided to different individuals on a role-specific basis. For example, administrative personnel may only have access to patient appointments at a fixed workstation at their office, whereas physicians may receive patient appointments around the clock on a calendar application of their mobile device.

In some implementations, the particular data that is provided for a given notification is a function of the delivery channel. For example, the general practitioner may have a secure office computer as well as a less-secure mobile device. In scenario 100, the notification sent to the general practitioner's mobile device could be limited to an identification of the patient that was admitted to the emergency room. To determine the particular symptoms and treatments, the general practitioner may have to either enter a password into their mobile device to initiate an encrypted session, or go to their office and obtain the information from their work computer.

Example GUIs

FIGS. 6A and 6B illustrate exemplary GUIs that can be provided for user registration of subscription concepts. FIG. 6A illustrates a GUI 600 that can be employed to allow a user to select two predefined notification concepts, selected respectively from drop-down menus 601 and 602. For example, GUI 600 could be employed in advance of scenario 100 to allow the general practitioner to receive notification 118 at instance 3. In FIG. 6A, the general practitioner can select one predefined concept for "NSAIDS" and another predefined concept for "pain." If the general practitioner wishes to be notified on statistically-correlated concepts, the general practitioner can also select boxes 603 and 604, respectively. By selecting button 605, the general practitioner can submit a subscription message to the database which can then monitor the data in the database for updates that trigger a notification for the subscription.

FIG. 6B illustrates GUI 600 in a different configuration where a keyword concept replaces predefined concept 2. Here, GUI 600 is shown with a text entry block 606, where the general practitioner can enter a freeform keyword instead of selecting from an available predefined concept. For example, by entering the keyword "fever" instead of the more general predefined concept "pain," the general practitioner can limit the notifications they receive to instances when their patients are admitted to the ER with a fever instead of for general pain. Note that in some implementations the keyword concept "fever" can be expanded to include a range of values, e.g., 101-108 degrees Fahrenheit body temperature, etc. Accordingly, method 500 can trigger a notification when an individual record in the transaction log reflects a body temperature in this range.

System Example

Figure 7:
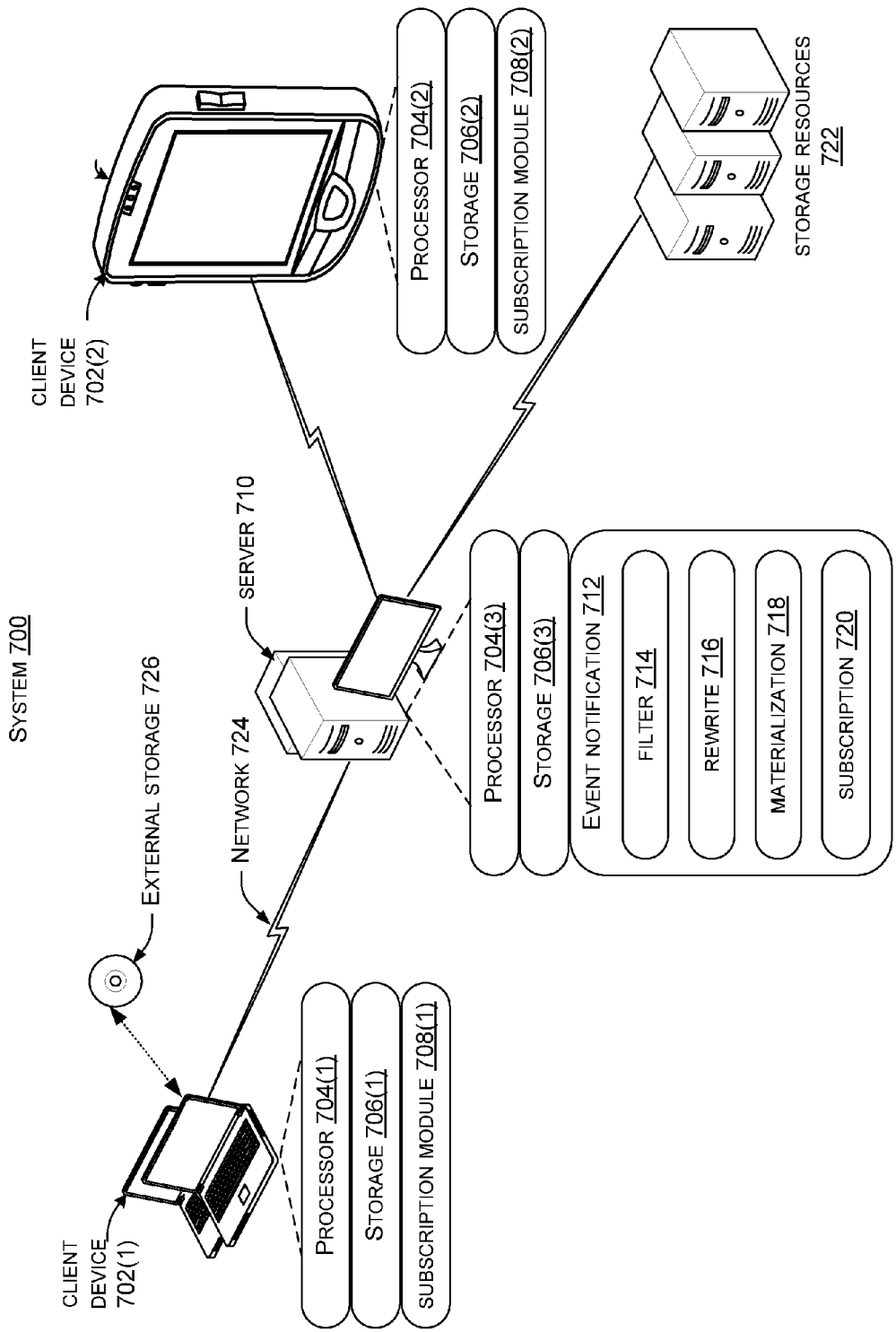
FIG. 7 shows an example of a system in accordance with some implementations of the present concepts.

FIG. 7 shows an example of a system 700. Example system 700 includes one or more client device(s) 702, shown as a notebook client device 702(1) and a mobile client device 702(2), respectively. In this case, client device(s) 702 can each include a processor 704, storage 706, and a subscription module 708. (A suffix '(1)' is utilized to indicate an occurrence of these modules on client device 702(1) and a suffix '(2)' is utilized to indicate an occurrence on client device 702(2)).

System 700 can also include one or more server(s) 710. Server(s) 710 can be a computing device that also includes a processor 704(3) and storage 706(3). Note the suffix (3) is used to indicate an occurrence of a processor or storage on server 710. Server 710 can also include an event notification module 712, which can include submodules such as filter module 714, rewrite module 716, materialization module 718, and/or subscription module 720. System 700 can also include storage resources 722, which can include one or more storage devices configured to store the physical database tables mentioned above.

Client device(s) 702, server 710, and storage resources 722 can communicate over one or more networks 724, such as, but not limited to, the Internet. Modules 708 and 712-720 can be implemented as software, hardware, and/or firmware. Processor(s) 704 can execute data in the form of computer-readable instructions to provide a functionality. Data, such as computer-readable instructions, can be stored on storage 706. The storage can include any one or more of volatile or non-volatile memory, hard drives, and/or optical storage devices (e.g., CDs, DVDs etc.), among others. Client device(s) 702 and server 710 can also be configured to receive and/or generate data in the form of computer-readable instructions from an external storage 726.

Examples of external storage 726 can include optical storage devices (e.g., CDs, DVDs etc.), hard drives, and flash storage devices (e.g., memory sticks or memory cards), among others. In some cases, modules discussed herein can be installed on the client devices or server during assembly or at least prior to delivery to the user. In other scenarios, the modules discussed herein can be installed by the user after delivery, such as a download available over network 724 and/or from external storage 726. The modules discussed herein can be manifest as freestanding applications, application parts and/or part of the computing device's operating system.

Collectively, the modules discussed herein can achieve the functionality described above relative to FIGS. 1-6. For example, filter module 714 can be configured to implement method 200, rewrite module 716 can be configured to implement method 300, materialization module 718 can be configured to implement method 400, and subscription module 720 can be configured to implement method 500. It is worth noting that in some instances, the client devices or servers can comprise multiple computing devices or machines, such as in a distributed environment. In such a configuration, methods 200-500 can be implemented using distributed processing across the multiple computing devices or machines.

The terms "computer," "client device," "server" and "computing device" as used herein can mean any type of device that has some amount of processing capability and/or storage capability. Processing capability can be provided by one or more processors that can execute data in the form of computer-readable instructions to provide a functionality. Data, such as computer-readable instructions, can be stored on storage. The storage can be internal and/or external to the computing device. The storage can include any one or more of volatile or non-volatile memory, hard drives, flash storage devices, and/or optical storage devices (e.g., CDs, DVDs etc.), among others. As used herein, the term "computer-readable media" can include transitory and non-transitory computer-readable instructions. In contrast, the term "computer-readable storage media" excludes transitory instances. Computer-readable storage media includes "computer-readable storage devices". Examples of computer-readable storage devices include volatile storage media, such as RAM, and non-volatile storage media, such as hard drives, optical discs, and flash memory, among others.

Examples of computing devices can include traditional computing devices, such as personal computers, cell phones, smart phones, personal digital assistants, or any of a myriad of ever-evolving or yet to be developed types of computing devices. Further, aspects of system 700 can be manifest on a single computing device or distributed over multiple computing devices.

Conclusion

The order in which the example methods are described is not intended to be construed as a limitation, and any number of the described blocks or steps can be combined in any order to implement the methods, or alternate methods. Furthermore, the methods can be implemented in any suitable hardware, software, firmware, or combination thereof, such that a computing device can implement the methods. In one case, the methods are stored on one or more computer-readable storage media as a set of instructions such that execution by one or more computing devices causes the one or more computing devices to perform the method.

Although techniques, methods, devices, systems, etc., pertaining to secure patient information handling are described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method performed by at least one computing device, the method comprising:
 creating a materialized view table based on one or more physical tables of a database storing a plurality of records;
 obtaining first temporal metadata associated with a first network message that was received over a network at a first time;
 obtaining second temporal metadata associated with a second network message that was received over the network at a second time that is later than the first time;
 identifying an interval during which a subset of the records of the database were altered, the interval being identified by the first temporal metadata and the second temporal metadata; and
 performing an update on the materialized view table while limiting the update to the subset of the records that were altered during the interval identified by the first temporal metadata and the second temporal metadata,
 wherein limiting the update to the subset of the records comprises using the first temporal metadata and the second temporal metadata to obtain a constrained set of primary keys that are used to extract the subset of the records.

2. The method according to claim 1, wherein performing the update on the materialized view table comprises deleting one or more rows from the materialized view table, the one or more deleted rows corresponding to one or more individual records of the subset.

3. The method according to claim 2, wherein performing the update on the materialized view table comprises reevaluating the one or more rows that are deleted from the materialized view table against the one or more physical tables of the database.

4. The method according to claim 1, wherein performing the update on the materialized view table comprises overwriting one or more rows of the materialized view table without deleting the one or more rows, the one or more overwritten rows corresponding to one or more individual records of the subset.

5. The method according to claim 1, further comprising:
 extracting the constrained set of primary keys from a queryable transaction log of ongoing changes to the database.

6. The method according to claim 5, wherein the queryable transaction log comprises a redo log.

7. The method according to claim 5, wherein the queryable transaction log comprises a change data capture (CDC) table.

8. One or more hardware computer-readable storage media comprising computer-readable instructions which, when executed by one or more computing devices, cause the one or more computing devices to perform acts comprising:
 maintaining a materialized view table using tables of a database, the database storing multiple records having associated primary keys;
 identifying individual records that have been altered in the tables by messages of a message pipeline during an interval of time, wherein the identifying comprises determining the interval of time using temporal metadata reflecting an order in which at least two of the messages of the message pipeline were communicated over a network;

using the temporal metadata reflecting the order in which the at least two of the messages were communicated to constrain which of the primary keys are used for an update of the materialized view table to a constrained set of individual primary keys, wherein the constrained set of individual primary keys correspond to the individual records that have been altered during the interval of time; and performing the update on the materialized view table using the constrained set of individual primary keys.

9. The one or more hardware computer-readable storage media according to claim 8, wherein the individual records that have been altered comprise medical records.

10. The one or more hardware computer-readable storage media according to claim 8, wherein the temporal metadata comprises message identifiers for the messages in the message pipeline.

11. The one or more hardware computer-readable storage media according to claim 10, wherein the message identifiers are sequential.

12. The one or more hardware computer-readable storage media according to claim 10, wherein the message identifiers are sequentially increasing such that individual messages with relatively higher message identifiers are received by the database over the network after other individual messages with relatively lower message identifiers.

13. The one or more hardware computer-readable storage media according to claim 8, the acts further comprising:

determining that changes to the multiple records include an ignorable change for the materialized view table; and not performing the identifying for the ignorable change.

14. The one or more hardware computer-readable storage media according to claim 13, wherein the ignorable change is an individual change to the tables that does not affect any columns that are returned by the materialized view table.

15. The one or more hardware computer-readable storage media according to claim 13, wherein the ignorable change is an individual change to the tables that does not affect any columns that are used as conditions by the materialized view table.

16. A system comprising:

one or more hardware processors; and one or more computer-readable memory devices or storage devices storing instructions which, when executed by the one or more processors, cause the one or more processors to:

access a materialized view table, wherein the materialized view table is created based on one or more physical tables of a database storing multiple records having associated database keys;

use temporal metadata associated with network messages of a message pipeline to select individual records that have been altered in the database during a particular interval of time, wherein the individual records are identified in the one or more physical tables by an associated constrained set of database keys that excludes at least some other database keys for other records that were not altered in the database during the particular interval of time;

rewrite a view query for the materialized view table using a filter condition that extracts the individual records having the associated constrained set of database keys; and execute the rewritten view query to update the materialized view table such that the materialized view table reflects the individual records that were altered in the database during the particular interval of time.

17. The system according to claim 16, wherein individual database keys are primary keys.

18. The system according to claim 16, wherein the instructions cause the one or more hardware processors to maintain the materialized view table periodically based on a set refresh interval.

19. The system according to claim 16, wherein the materialized view table reflects at least part of a personal health care record for a patient.

20. The system according to claim 16, embodied as a single computing device.

* * * * *